(12) United States Patent
Nakamura et al.

(10) Patent No.: US 11,213,472 B2
(45) Date of Patent: Jan. 4, 2022

(54) VEGFC PRODUCTION PROMOTER

(71) Applicant: Shiseido Company, Ltd., Tokyo (JP)

(72) Inventors: Mio Nakamura, Yokohama (JP);
Kentaro Kajiya, Yokohama (JP);
Shinichiro Haze, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 16/827,033

(22) Filed: Mar. 23, 2020

(65) Prior Publication Data

US 2020/0222294 A1    Jul. 16, 2020

Related U.S. Application Data

(60) Division of application No. 15/625,080, filed on Jun. 16, 2017, now Pat. No. 10,624,829, which is a continuation of application No. 14/431,837, filed as application No. PCT/JP2013/076416 on Sep. 27, 2013, now abandoned.

(30) Foreign Application Priority Data

Sep. 28, 2012   (JP) ................................ 2012-218612

(51) Int. Cl.
| | |
|---|---|
| *A61K 36/00* | (2006.01) |
| *A61K 8/49* | (2006.01) |
| *A61K 36/61* | (2006.01) |
| *A61K 8/37* | (2006.01) |
| *A61Q 19/08* | (2006.01) |
| *A61K 31/22* | (2006.01) |
| *A61K 31/351* | (2006.01) |
| *A61K 8/92* | (2006.01) |
| *A61K 36/738* | (2006.01) |
| *A61Q 19/06* | (2006.01) |
| *A61K 31/122* | (2006.01) |
| *A61Q 19/10* | (2006.01) |
| *A61Q 19/00* | (2006.01) |

(52) U.S. Cl.
CPC ............... *A61K 8/498* (2013.01); *A61K 8/37* (2013.01); *A61K 8/922* (2013.01); *A61K 31/122* (2013.01); *A61K 31/22* (2013.01); *A61K 31/351* (2013.01); *A61K 36/61* (2013.01); *A61K 36/738* (2013.01); *A61Q 19/06* (2013.01); *A61Q 19/08* (2013.01); *A61Q 19/007* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 4,206,090 A | 6/1980 | Schmitt | |
| 5,260,313 A | 11/1993 | Frome | |
| 6,574,504 B1 | 6/2003 | Mazaury et al. | |
| 2004/0235472 A1 | 11/2004 | Mita et al. | |
| 2008/0233219 A1 | 9/2008 | Karita | |
| 2009/0197939 A1 | 8/2009 | Walke et al. | |
| 2010/0196521 A1* | 8/2010 | Liu .................. | A61K 36/54 424/736 |
| 2010/0292509 A1 | 11/2010 | Kajiya et al. | |
| 2011/0257255 A1 | 10/2011 | McLellan et al. | |

FOREIGN PATENT DOCUMENTS

| | | |
|---|---|---|
| CN | 101619263 A | 1/2010 |
| CN | 101677973 A | 3/2010 |
| CN | 102151310 A | 8/2011 |
| FR | 2781162 A1 | 1/2000 |
| JP | 2005-298487 A | 10/2005 |
| JP | 2006-056845 A | 3/2006 |
| JP | 2006-241044 A | 9/2006 |
| JP | 2008-189609 A | 8/2008 |
| JP | 2013-155122 A | 8/2013 |
| WO | WO 99/26589 A2 | 6/1999 |
| WO | WO 2007/026645 A1 | 3/2007 |
| WO | WO 2009/093534 A1 | 7/2009 |
| WO | WO 2011/034591 A1 | 3/2011 |

OTHER PUBLICATIONS

Boskabody et al., Pharmacalogical Effects of *Rosa Damascena*, Iranian Journal of Basic Medicinal Sciences, Jul.-Aug. 2011, 14(4):295-307.
Database GNPD, Online, MINTEL, Diptyque, "Eau de Toilette," Dec. 2011, XP002753760.
Kentaro Kajiya et al., "A Novel Mechanism of Cutaneous Photo-Aging Mediated by the Impairment of Lymphatic Function and the Protective Role of a Lymphatic-promoting Compound," Fragrance Journal, Nov. 2009, Nov. 2009, p. 91.
Lymphedema from Wkipedia, accessed on Aug. 27, 2018, 1-12.
Kreis et al., "Chiral compounds of essential oils, Part XII. Authenticity control of rose oils, using enantioselective multidimensional gas chromatography," Flavour and Fragrance Journal, 1992, 7(4):199-203.
Nonato et al., "Anti-inflammatory properties of rose oxide," International Immunopharmacology, Nov. 1, 2012,14(4):779-784.
Saaristo et al., "Vascular endothelial growth factor-C gene therapy restores lymphatic flow across incision wounds," The FASEB Journal, 2004, 18(14):1707-1709.
Shiseido, Hana no Hoko Seibun ni Rinpa-kan no Kyoka Sayo o Hakken, Nikkei Biotechnology, Online, https://bio.nikkelbo.co.jp/article/news/20131027/171678/, published Oct. 28, 2013, 1 page.

(Continued)

*Primary Examiner* — Qiuwen Mi
(74) *Attorney, Agent, or Firm* — Foley & Lardner LLP

(57) ABSTRACT

The purpose of this invention is to find a novel fragrance component effective for prevention or control of swelling, lymphedema, skin aging or obesity from the viewpoint of activation of lymph vessel function by promotion of the expression of VEGFC. This invention provides a swelling improving agent, lymph vessel activator and VEGFC production promoter characterized by containing one or a plurality of components selected from the group consisting of rose oxide, citronellyl acetate and niaouli oil.

3 Claims, 1 Drawing Sheet

(56) References Cited

OTHER PUBLICATIONS

Shiseido, Rinpa-ken no Kino Teika ga Shiwa Keisei no Gen'in de aru Koto o Kaimei, Fragrance Journal, Apr. 2008, Apr. 2008, p. 7.
Shiseido, Tennen no Bara no Kaori Seibun no Hifu Seiri Koka o Hakken, Nikkan Kogyo Shinbun, Business Line, http://www.nikkan.co.jp/news/nkx1020131030ceba.html, published Oct. 30, 2013, 2 pages.
Souza et al., "Selecao de extratos brutos de plantas com atividade antiobesidade," Revista Brasiliera De Plantas Medicinais, RBPM= Brazilian Journal of Medicinal Plants, Jan. 1, 2012, 14(4):643-648, with English abstract on first page.

* cited by examiner

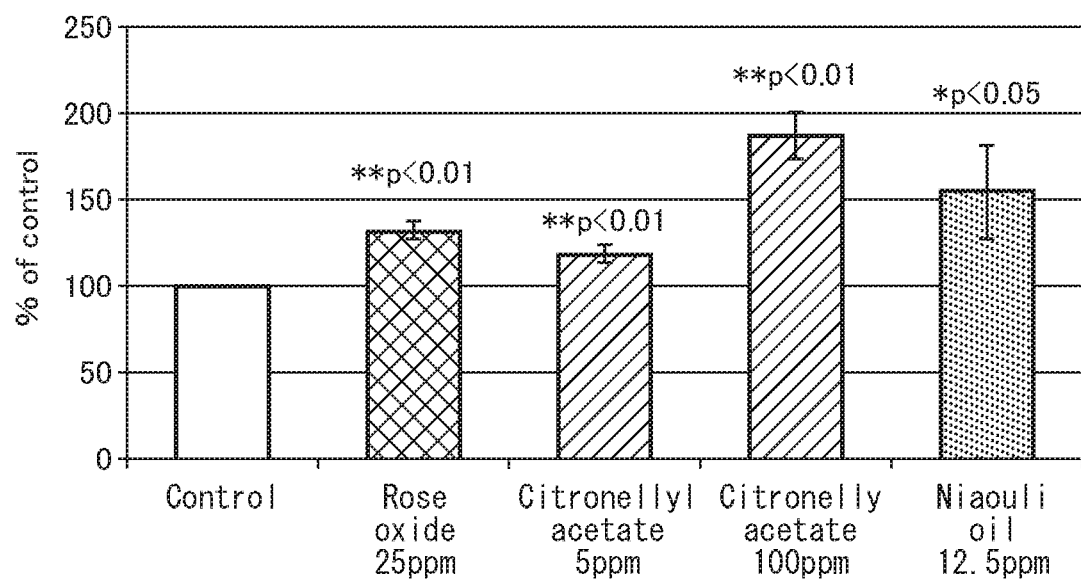

VEGFC PRODUCTION PROMOTER

CROSS-REFERENCE TO RELATED APPLICATIONS

This application is a Divisional of U.S. application Ser. No. 15/625,080, filed Jun. 16, 2017, which is a Continuation of U.S. application Ser. No. 14/431,837, which is the U.S. National Stage application of PCT/JP2013/076416, filed Sep. 27, 2013, which claims priority from Japanese application JP 2012-218612, filed Sep. 28, 2012.

TECHNICAL FIELD

The present invention relates to an agent for improving swelling, lymphedema, wrinkles or obesity by promoting activation of lymphatic vessel function by inducing expression of vascular endothelial growth factor C (VEGFC).

BACKGROUND ART

The cutaneous vasculature is present in the dermis and is composed of blood vessels and lymph vessels. In order to maintain homeostasis, tissue fluid that has migrated outside blood vessels must be recirculated to veins. Veins present in skin effectively send blood to the body's core. However, veins per se lack the ability to incorporate tissue fluid. On the basis of this as well, tissue that incorporates tissue fluid, namely lymph vessels, have come to be understood to be an essential structure in the skin as well.

Lymph vessels fulfill an important role in order to maintain the microenvironment surrounding tissue in a constant state by recovering unwanted substances present in skin as well as water and protein constantly escaping from blood vessels. In addition, it has also come to be thought to fulfill the role of demonstrating resistance to infectious factors and external factors from the outside world by mediating the transport of T lymphocytes.

Known examples of pathological states associated with lymph vessel dysfunction include symptoms such as swelling and lymphedema (Non-Patent Document 1: Jusilla, L. & Alitalo, K. (2002), Physiol. Rev. 82, 673-700). In addition, lymph vessel function has also been determined to fulfill an important role in not only swelling, but also photoaging (wrinkle formation) of skin accompanying exposure to ultraviolet rays (Non-Patent Document 2: Kajiya, K. & Detmar, M. (2006), J. Invest. Dermatol. 126, 919-21).

According to previous research, VEGFR-3 has been identified as a transmembrane receptor specifically present in lymph vessels, and VEGFC and VEGFD have been found to be ligands thereof. VEGFC activates the function of lymph vessels by promoting the proliferation, migration and lumen formation of lymphatic endothelial cells by acting on lymph vessels (Non-Patent Document 1: Jusilla, L. & Alitalo, K. (2002), Physiol. Rev. 82, 673-700). In addition, possibilities are being sought for gene therapy involving the application of VEGFC to the pathological state of swelling in the form of edema (Non-Patent Document 3: Saaristo, A., Tammela, T., Timonen, J., Yla-Herttuala, S., Tukianen, E., Asko-Seljavaara, S. & Alitalo, K. (2004), Faseb. J. 18, 1707-9).

Recently, mutant mice having a genetic mutation that causes lymph vessel dysfunction are known to exhibit obesity as they mature. Findings have been obtained regarding the mechanism by which abnormalities in lymph vessel formation and function result in obesity that indicate that lymphatic fluid flowing through lymph vessels promotes differentiation of mast cell progenitors into fat (Patent Document 4: Harvey, N. L., et al., Nat. Genet. 2005, 37, 1072-81). In other words, functional abnormalities of lymph vessels have been reported to cause escape of lymphatic fluid outside lymph vessels leading to differentiation into fat and eventually the onset of obesity. Thus, VEGFC promoter is expected to function as an obesity preventive or therapeutic agent that functionally regenerates lymph vessels.

The VEGF gene family consists of VEGF-A through VEGF-E. Among these, VEGFB and VEGFE have been identified as factors that act only on blood vessels. Although VEGFA is present in the skin and acts on lymph vessels, it is known to be a factor that conversely exacerbates the function of lymph vessels (Non-Patent Document 5: Nagy, J. A., Vasile, E., Feng, D., Sundberg, C., Brown, L. F., Detmar, M. J., Lawitts, J. A., Benjamin, L., Tan, X., Manseau, E. J., Dvorak, A. M. & Dvorak, H. F. (2002), J. Exp. Med. 196, 1497-506).

In the skin, although VEGFD has been reported to be present in trace amounts in the dermis, since VEGFD knockout mice do not exhibit any formational or functional abnormalities of skin lymph vessels whatsoever, VEGFD is not thought to be a factor that is essential for lymph vessel formation in skin (Non-Patent Document 6: Baldwin, M. E., Halford, M. M., Roufail, S., Williams, R. A., Hibbs, M. L., Grail, D., Kubo, H., Stacker, S. A. & Achen, M. G. (2005), Mol. Cell. Biol. 25, 2441-9). On the other hand, VEGFC in the skin is strongly expressed in the epidermis. Mice in which VEGFC has been strongly expressed in the epidermis exhibit an increase in the number of lymph vessels present in the dermis (Non-Patent Document 7: Jeltsch, M., Kaipeinen, A., Joukov, V., Meng, X., Lakso, M., Rauvala, H., Swartz, M., Fukumura, D., Jain, R. K. & Alitalo, K. (1997), Science 276, 1423-5), while on the other hand, when the effects of VEGFC in the epidermis were blocked by highly expressing neutralizing antibody of a VEGFC receptor in the form of VEGFR-3 in the epidermis, findings were obtained that indicated a dramatic decrease in the number of lymph vessels in the dermis along with the onset of edema (Non-Patent Document 8: Makinen, T., Jussila, L., Veikkola, T., Karpanen, T., Kettunen, M. I., Pulkkanen, K. J., Kauppinen, R., Jackson, D. G., Kubo, H., Nishikawa, S., Yla-Herttuala, S. & Alitalo, K. (2001), Nat. Med. 7, 199-205). On the basis thereof, it has been determined that the function of lymph vessels present in skin dermis is controlled by VEGFC expressed in the epidermis, and that swelling (edema) occurs as a result of VEGFC no longer functioning.

It has been previously reported that specific terpenoids and derivatives thereof have a VEGF production-promoting action and are useful as wound healing agents, hair restorers and hair growth agents and external skin agents having ameliorative effects on skin color (Patent Document 1), and that plant extracts in the manner of apricot kernel extract, *ginseng* extract, Japanese valerian extract, *crataegus* fruit extract, melilot extract, white nettle extract and orris root extract have VEGFC production-promoting action (Patent Document 2).

PRIOR ART DOCUMENTS

Patent Documents

[Patent Document 1] Japanese Unexamined Patent Publication No. 2004-2258
[Patent Document 2] Japanese Unexamined Patent Publication No. 2008-189609

Non-Patent Documents

[Non-Patent Document 1] Physiol. Rev. 82, 673-700 (2002)
[Non-Patent Document 2] J. Invest. Dermatol. 126, 919-21 (2006)
[Non-Patent Document 3] Faseb. J. 18, 1707-9 (2004)
[Non-Patent Document 4] Nat. Genet. 37, 1072-81 (2005)
[Non-Patent Document 5] J. Exp. Med. 196, 1497-506 (2002)
[Non-Patent Document 6] Mol. Cell. Biol. 25, 2441-9 (2005)
[Non-Patent Document 7] Science 276, 1423-5 (1997)
[Non-Patent Document 8] Nat. Med. 7, 199-205 (2001)

DISCLOSURE OF THE INVENTION

Problems to be Solved by the Invention

An object of the present invention is to discover a novel component that is effective for preventing or controlling swelling, lymphedema, wrinkle formation or obesity by activating lymph vessel function by inducing expression of VEGFC.

Means for Solving the Problems

As a result of conducting extensive studies towards solving the aforementioned problems, the inventor of the present invention found that aromatic components in the manner of rose oxide, citronellyl acetate and niaouli oil induce expression of VEGFC. In other words, the inventor of the present invention found that these components that induce expression of VEGFC are extremely useful for preventing or inhibiting swelling, lymphedema, formation of wrinkles caused by photoaging of the skin accompanying exposure to ultraviolet rays, or obesity by promoting activation of lymph vessel function.

The constitution of the present invention is as described below.

[1] A VEGFC production promoter containing one or more components selected from the group consisting of rose oxide, citronellyl acetate and niaouli oil.

[2] A lymphangiogenesis and/or lymphatic function promoter containing one or more components selected from the group consisting of rose oxide, citronellyl acetate and niaouli oil.

[3] A swelling ameliorant containing one or more components selected from the group consisting of rose oxide, citronellyl acetate and niaouli oil.

[4] A lymphedema ameliorant containing one or more components selected from the group consisting of rose oxide, citronellyl acetate and niaouli oil.

[5] A wrinkle ameliorant containing one or more components selected from the group consisting of rose oxide, citronellyl acetate and niaouli oil.

[6] An obesity ameliorant containing one or more components selected from the group consisting of rose oxide, citronellyl acetate and niaouli oil.

[7] The VEGFC production promoter described in [1], which prevents or inhibits swelling.

[8] The lymphangiogenesis and/or lymphatic function promoter described in [2], which prevents or inhibits swelling.

[9] The VEGFC production promoter described in [1], which prevents or inhibits lymphedema.

[10] The lymphangiogenesis and/or lymphatic function promoter described in [2], which prevents or inhibits lymphedema.

[11] The VEGFC production promoter described in [1], which prevents or inhibits wrinkle formation.

[12] The lymphangiogenesis and/or lymphatic function promoter described in [2], which prevents or inhibits wrinkle formation.

[13] The VEGFC production promoter described in [1], which prevents or inhibits obesity.

[14] The lymphangiogenesis and/or lymphatic function promoter, which prevents or inhibits obesity.

[15] An aesthetic or therapeutic method for preventing or inhibiting swelling, lymphedema, wrinkles formation and/or obesity, comprising applying the VEGFC production promoter described in [1] to the skin of a subject requiring prevention or inhibition of these conditions.

[16] An aesthetic or therapeutic method for preventing or inhibiting swelling, lymphedema, wrinkles formation and/or obesity, comprising applying the lymphangiogenesis and/or lymphatic function promoter described in [2] to the skin of a subject requiring prevention or inhibition of these conditions.

[19] A use of the VEGFC production promoter described in [1] for preventing or inhibiting swelling, lymphedema, wrinkle formation and/or obesity.

[20] A use of the lymphangiogenesis and/or lymphatic function promoter described in [2] for preventing or inhibiting swelling, lymphedema, wrinkle formation and/or obesity.

Effects of the Invention

Expression of vascular endothelial growth factor C (VEGFC) in the body is induced and activation of lymph vessel function is promoted by applying one or more components selected from the group consisting of rose oxide, citronellyl acetate and niaouli oil. This action makes it possible to prevent or improve swelling, lymphedema, wrinkle formation or obesity.

BRIEF DESCRIPTION OF THE DRAWINGS

FIG. 1 is a graph showing the VEGFC-inducing activity of rose oxide, citronellyl acetate and niaouli oil.

MODE FOR CARRYING OUT THE INVENTION

Definitions

The term "swelling" in the present description is used in the same context as "edema", and refers to a state observed in subcutaneous tissue in which tissue fluid or lymphatic fluid accumulates in cells, intercellular space or body cavities due to some cause. Moreover, the term "lymphedema" in the present description refers to a state in which tissue fluid accumulates in distal regions due to occlusion of lymph vessels.

As is described in detail in the subsequent examples, screening for agents that induce a lymph vessel activating factor in the form of VEGFC was carried out by allowing various types of candidate aromatics to act on human epidermis-derived cultured cells in the form of HaCaT cells, quantifying VEGFC, and selecting aromatics having VEGFC-inducing activity as active ingredients by using the amount of VEGFC as an indicator of VEGFC-inducing activity.

As a result, rose oxide, citronellyl acetate and niaouli oil were found to induce VEGFC.

*Rose Oxide

Rose oxide is an organic compound that has the chemical structure indicated below and has two asymmetric carbons within a molecule thereof.

[Chemical Formula 1]

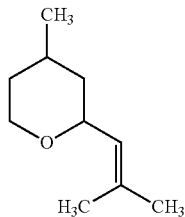

Rose oxide has a sweet fragrance like that of roses, and is used as a pyran-based, monoterpene-based aromatic in cosmetics and soaps. It can be obtained from roses, rose oil, apricots and peppermint in nature, and has a plurality of geometrical and optical isomers. Industrially, it is obtained in equal amounts of the cis-form and trans-form by reducing allyl hydroperoxides, which are obtained by photooxidation of citronellol, to obtain a diol followed by closing the ring with sulfuric acid. Commercial products available as aromatics consist primarily of the cis racemic form.

*Citronellyl Acetate

Citronellyl acetate is an organic compound represented by the following chemical formula that is in the form of a colorless, clear liquid at normal temperature.

[Chemical Formula 2]

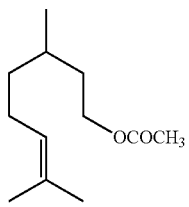

$C_{12}H_{22}O_2 = 198.31$

It is used as an aromatic of foods and cosmetics since it has a unique fragrance that resembles that of roses or lavender. In nature, it is contained in essential oils such as citronella oil or geranium oil, and is synthesized industrially from citronellol.

*Niaouli Oil

Niaouli oil is an essential oil collected from the leaves or branches of *Melaleuca virdiflora*, a plant of the Myrtaceae family found in the Pacific region such as in Indonesia, Australia and New Zealand, and on Madagascar Island in the Indian Ocean. It has bactericidal action and is used in cosmetics, soaps or bath additives and the like.

The aforementioned aromatic components according to the present invention are extremely useful for promoting the formation and function of lymph vessels. Symptoms accompanying lymph vessel dysfunction include not only swelling and lymphedema, but also photoaging (such as wrinkle formation) of skin accompanying exposure to ultraviolet rays and obesity. The agent according to the present invention is effective for preventing or inhibiting swelling and lymphedema along with photoaging of the skin accompanying exposure to ultraviolet rays and obesity. Moreover, the aforementioned aromatic components are also thought to be useful in the treatment of congenital lymphedema.

Photoaging of the skin refers to a change in the appearance and function of skin typically observed as a result of repeated exposure to sunlight. Constituent elements of sunlight in the form of ultraviolet (UV) rays, and particularly ultraviolet B rays (referred to as UVB rays having a wavelength of 290 nm to 320 nm), are the primary cause of photoaging. The exposure level of UVB required to cause photoaging is currently not known. However, repeated exposure to UVB at a level that causes erythema or sunburn normally leads to photoaging. In clinical terms, photoaging can be identified by, for example, rough skin, wrinkle formation, colored spots, pale color, sagging skin, onset of telangiectasia, mole formation, onset of purpura, increased susceptibility to wounds, atrophy, appearance of regions of fibrotic pigment removal and the onset of premalignant and malignant tumors. Photoaging usually occurs in skin that has been routinely exposed to sunlight, such as that of the face, ears, head, neck and hands.

The dosage, administration form and dosage form of the VEGFC production promoter, lymphangiogenesis and/or lymphatic function promoter, swelling ameliorant, lymphedema ameliorant, wrinkle ameliorant or obesity ameliorant of the present invention (to also be referred to as the "present agent") can be suitably determined corresponding to the purpose of use thereof. For example, the aromatic component in the present agent is typically incorporated at 0.0001% by weight to 0.1% by weight, preferably at 0.001% by weight to 0.01% by weight, and optimally at 0.005% by weight to 0.01% by weight based on the total weight of the drug. Although there are no particular limitations on the administration form of the present agent, and may be administered orally, parenterally, externally or by inhaling and the like, it is preferably a skin external agent from the viewpoint of being able to act both by inhaling and transcutaneously. Examples of dosage forms include cosmetics such as perfumes, colognes, shampoos, rinses, skin care products, body shampoos, body rinses, body powders, air fresheners, deodorants, bath additives, lotions, creams, soaps, toothpastes or aerosol products, and other forms commonly used in aromatics. Moreover, the present agent can also be used in pharmaceuticals such as inhalants.

In addition, the present agent can also suitably incorporate as necessary other components in addition to the aforementioned essential components such as components normally used in foods or pharmaceuticals such as external skin agents in the manner of skin whitening agents, moisturizers, antioxidants, oily components, ultraviolet absorbers, surfactants, thickeners, alcohols, powdered components, coloring agents, aqueous components, water or various types of skin nutrients.

In addition, other components can also be suitably incorporated, examples of which include sequestering agents such as disodium edetate, trisodium edetate, sodium citrate, sodium polyphosphate, sodium metaphosphate or gluconic acid, hot water extracts such as caffeine, tannin, verapamil, tranexamic acid and derivatives thereof, licorice extract, glabridin or quince fruit extract, various types of natural herbs, drugs such as tocopherol acetate, glycyrrhizic acid and derivatives thereof, and salts thereof, skin whitening agents such as vitamin C, magnesium ascorbyl phosphate, ascorbic acid glucoside, albumin or kojic acid, sugars such as glucose, fructose, mannose, sucrose or trehalose, and vitamin A such as retinoic acid, retinol, retinol acetate or retinol palmitate.

EXAMPLES

Human-derived cultured cells in the form of HaCaT cells (German Cancer Research Center, Heidelberg, Germany) were cultured in DMEM medium (Gibco Low Glucose DMEM™, Life Technologies Inc.) containing 10% FBS (Standard Fetal Bovine Serum, Hyclone Laboratories Inc.) and disseminated in a 24-well plate to $15 \times 10^4$ cells/well. The medium was replaced with serum-free DMEM 24 hours after dissemination followed by culturing for 24 hours. Subsequently, each aromatic dissolved in ethanol was added (aromatic final concentration: 0.001% to 0.01%). Ethanol was used as a control. The culture supernatant was recovered after culturing for 48 hours and the amount of VEGFC in the culture supernatant was quantified in accordance with the protocol of an ELISA kit (Quanikine® Human VEGF-C Immunoassay (R&D Systems Inc., Minneapolis, Minn.)). In addition, alamar blue (TREK Diagnostic Systems, Inc., Cleveland, US) was added to the cells after recovering the culture supernatant followed by measuring the number of cells based on their fluorescence intensity (Ex: 544 nm, Em: 590 nm). The amount of VEGFC in the supernatant was divided by fluorescence intensity, and the relative VEGFC-inducing activity per cell based on a value of 100 for the control (ethanol) is shown in FIG. 1. The synthetic aromatics of rose oxide and citronellyl acetate along with the natural aromatic, niaouli oil (supplier: Biolandes Inc.), demonstrated VEGFC-inducing activity as shown in FIG. 1 without demonstrating cytotoxicity at each concentration.

FORMULATION EXAMPLES

Although the following indicates formulation examples of the VEGFC production promoter of the present invention, carrying out the present invention is not limited to the following examples.

Beauty Wash

|  | Formula | (wt %) |
|---|---|---|
| (1) | Glycerin | 2.0 |
| (2) | Dipropylene glycol | 2.0 |
| (3) | PEG-60 hydrogenated castor oil | 0.3 |
| (4) | Trimethylglycine | 0.1 |
| (5) | Preservative | As suitable |
| (6) | Chelating agent | As suitable |
| (7) | Dye | As suitable |
| (8) | VEGFC production promoter of present invention: Rose oxide | 0.05 |
| (9) | Purified water | Balance |

Beauty Wash

|  | Formula | (wt %) |
|---|---|---|
| (1) | Alcohol | 30.0 |
| (2) | Butylene glycol | 4.0 |
| (3) | Glycerin | 2.0 |
| (4) | PPG-13-decyltetradeceth-24 | 0.3 |
| (5) | Octyl methoxycinnamate | 0.1 |
| (6) | Menthol | 0.2 |
| (7) | Tocopherol acetate | 0.1 |
| (8) | Chelating agent | As suitable |
| (9) | Dye | As suitable |
| (10) | VEGFC production promoter of present invention: Niaouli oil | 0.1 |
| (11) | Purified water | Balance |

Milky Lotion

|  | Formula | (wt %) |
|---|---|---|
| (1) | Stearic acid | 2.0 |
| (2) | Cetyl alcohol | 1.5 |
| (3) | Vaseline | 4.0 |
| (4) | Squalane | 5.0 |
| (5) | Glycerol tri-2-ethylhexanoate | 2.0 |
| (6) | Sorbitan monooleate | 2.0 |
| (7) | Dipropylene glycol | 5.0 |
| (8) | PEG1500 | 0.3 |
| (9) | Triethanolamine | 0.1 |
| (10) | Preservative | As suitable |
| (11) | VEGFC production promoter of present invention: Citronellyl acetate | 0.01 |
| (12) | Purified water | Balance |

Milky Lotion

|  | Formula | (wt %) |
|---|---|---|
| (1) | Ethyl alcohol | 10.0 |
| (2) | Cyclomethicone | 0.1 |
| (3) | Butylene glycol | 5.0 |
| (4) | Dimethicone | 3.0 |
| (5) | Glycerin | 0.1 |
| (6) | Menthol | 1.0 |
| (7) | Trimethylsiloxycinnamic acid | 0.1 |
| (8) | Caffeine | 1.0 |
| (9) | Trimethylglycine | 1.0 |
| (10) | Xanthan gum | 0.001 |
| (11) | Hydroxyethyl cellulose | 0.1 |
| (12) | Fermented soybean extract | 1.0 |
| (13) | Lauryl betaine | 0.5 |
| (14) | Carbomer | 0.2 |
| (15) | Chelating agent | As suitable |
| (16) | Para-hydroxybenzoate | As suitable |
| (17) | Benzoic acid | As suitable |
| (18) | VEGFC production promoter of present invention: Rose oxide | 0.01 |
| (19) | Iron oxide | As suitable |
| (20) | Potassium hydroxide | 0.05 |
| (21) | Dicalcium glycyrrhizinate | 0.01 |
| (22) | Pyridoxine hydrochloride | 0.01 |
| (23) | Ascorbic acid glucoside | 0.01 |
| (24) | Arbutin | 3.0 |
| (25) | Saxifraga stolonifera extract | 0.1 |
| (26) | Water | Balance |

Milky Lotion

|  | Formula | (wt %) |
|---|---|---|
| (1) | Butylene glycol | 4.0 |
| (2) | Propylene glycol | 4.0 |
| (3) | Carbomer | 0.2 |
| (4) | Potassium hydroxide | 0.2 |
| (5) | Behenic acid | 0.5 |
| (6) | Stearic acid | 0.5 |
| (7) | Isostearic acid | 0.5 |
| (8) | Glyceryl stearate | 1.0 |
| (9) | Glyceryl isostearate | 1.0 |
| (10) | Behenyl alcohol | 0.5 |
| (11) | Squalane | 5.0 |
| (12) | Trioctanoin | 3.0 |
| (13) | Phenyl trimethicone | 2.0 |
| (14) | Batyl alcohol | 0.5 |
| (15) | Dicalcium glycyrrhizinate | 0.01 |
| (16) | Preservative | As suitable |
| (17) | Chelating agent | As suitable |
| (18) | Pigment | As suitable |
| (19) | VEGFC production promoter of present invention: Niaouli oil | 0.15 |
| (20) | Purified water | Balance |

Cream

| | Formula | (wt %) |
|---|---|---|
| (1) | Glycerin | 10.0 |
| (2) | Butylene glycol | 5.0 |
| (3) | Carbomer | 0.1 |
| (4) | Potassium hydroxide | 0.2 |
| (5) | Stearic acid | 2.0 |
| (6) | Glyceryl stearate | 2.0 |
| (7) | Glyceryl isostearate | 2.0 |
| (8) | Vaseline | 5.0 |
| (9) | Preservative | As suitable |
| (10) | Antioxidant | As suitable |
| (11) | VEGFC production promoter of present invention: Citronellyl acetate | 0.02 |
| (12) | Purified water | Balance |
| (13) | Chelating agent | As suitable |
| (14) | Pigment | As suitable |
| (15) | Stearyl alcohol | 2.0 |
| (16) | Behenyl alcohol | 2.0 |
| (17) | Hydrogenated palm oil | 2.0 |
| (18) | Squalane | 10.0 |
| (19) | Potassium 4-methoxysalicylate | 3.0 |

Cream

| | Formula | (wt %) |
|---|---|---|
| (1) | Glycerin | 3.0 |
| (2) | Dipropylene glycol | 7.0 |
| (3) | Polyethylene glycol | 3.0 |
| (4) | Glyceryl stearate | 3.0 |
| (5) | Glyceryl isostearate | 2.0 |
| (6) | Stearyl alcohol | 2.0 |
| (7) | Behenyl alcohol | 2.0 |
| (8) | Liquid paraffin | 7.0 |
| (9) | Cyclomethicone | 3.0 |
| (10) | Dimethicone | 1.0 |
| (11) | Octyl methoxycinnamate | 0.1 |
| (12) | Sodium hyaluronate | 0.05 |
| (13) | Preservative | As suitable |
| (14) | Antioxidant | As suitable |
| (15) | VEGFC production promoter of present invention: Rose oxide | 0.02 |
| (16) | Purified water | Balance |
| (17) | Chelating agent | As suitable |
| (18) | Pigment | As suitable |

Gel

| | Formula | (wt %) |
|---|---|---|
| (1) | Ethyl alcohol | 10.0 |
| (2) | Glycerin | 5.0 |
| (3) | Butylene glycol | 5.0 |
| (4) | Carbomer | 0.5 |
| (5) | Aminomethyl propanol | 0.3 |
| (6) | PEG-60 hydrogenated castor oil | 0.3 |
| (7) | Menthol | 0.02 |
| (8) | Preservative | As suitable |
| (9) | Chelating agent | As suitable |
| (10) | VEGFC production promoter of present invention: Citronellyl acetate | 0.01 |
| (11) | Purified water | Balance |

Aerosol

| | Formula | (wt %) |
|---|---|---|
| (1) | Glycerin | 2.0 |
| (2) | Dipropylene glycol | 2.0 |
| (3) | PEG-60 hydrogenated castor oil | 2.0 |
| (4) | HPPCD | 1.0 |
| (5) | Preservative | As suitable |
| (6) | Chelating agent | As suitable |
| (7) | Dye | As suitable |
| (8) | VEGFC production promoter of present invention: Niaouli oil | 0.1 |
| (9) | Purified water | As suitable |
| (10) | LPG | Balance |

Aerosol

| | Formula | (wt %) |
|---|---|---|
| (1) | Ethanol | 60.0 |
| (2) | Methyl lactate | 0.1 |
| (3) | Sodium lactate | 0.1 |
| (4) | Tocopherol acetate | 0.01 |
| (5) | Lactic acid | 0.01 |
| (6) | Caffeine | 0.01 |
| (7) | Fennel extract | 1.0 |
| (8) | Witch hazel extract | 1.0 |
| (9) | Houttuynia cordata extract | 1.0 |
| (10) | Dipropylene glycol | 1.0 |
| (11) | Nitrogen gas | 0.0 |
| (12) | Polyoxyethylene-polyoxypropylene decyl tetradecyl ether | 1.0 |
| (13) | Butylene glycol | 2.0 |
| (14) | Tocopherol | 0.05 |
| (15) | VEGFC production promoter of present invention | 0.01 |
| (16) | PEG-60 hydrogenated castor oil | 0.1 |
| (17) | Water | Balance |

Fragrance

| | Formula | (wt %) |
|---|---|---|
| (1) | Alcohol | 75.0 |
| (2) | Purified water | Balance |
| (3) | Dipropylene glycol | 5.0 |
| (4) | VEGFC production promoter of present invention: Citronellyl acetate | 1.0 |
| (5) | Antioxidant | 8.0 |
| (6) | Pigment | As suitable |
| (7) | Ultraviolet absorber | As suitable |

Bath Additive

| | Formula | (wt %) |
|---|---|---|
| (1) | Sodium sulfate | 45.0 |
| (2) | Sodium bicarbonate | 45.0 |
| (3) | Lavender oil | 9.0 |
| (4) | VEGFC production promoter of present invention: Niaouli oil | 1.0 |

Massage Oil

| | Formula | (wt %) |
|---|---|---|
| (1) | Erythritol | 2.0 |
| (2) | Caffeine | 5.0 |
| (3) | Cork tree bark extract | 3.0 |
| (4) | Glycerin | 50.0 |
| (5) | Carboxyvinyl polymer | 0.4 |
| (6) | Polyethylene glycol 400 | 30.0 |
| (7) | Trisodium edetate | 0.1 |

|  | Formula | (wt %) |
|---|---|---|
| (8) | Polyoxylene (10) methylpolysiloxane copolymer | 2.0 |
| (9) | Squalane | 1.0 |
| (10) | Sodium hydroxide | 0.15 |
| (11) | VEGFC production promoter of present invention: Rose oxide | 0.01 |

Massage Cream

|  | Formula | (wt %) |
|---|---|---|
| (1) | Solid paraffin | 5.0 |
| (2) | Beeswax | 10.0 |
| (3) | Vaseline | 15.0 |
| (4) | Liquid paraffin | 41.0 |
| (5) | 1,3-butyleneglycol | 4.0 |
| (6) | Glycerin monostearate | 2.0 |
| (7) | POE(20) sorbitan monolaurate | 2.0 |
| (8) | Borax | 0.2 |
| (9) | Caffeine | 2.0 |
| (10) | Preservative | As suitable |
| (11) | Antioxidant | As suitable |
| (12) | VEGFC production promoter of present invention: Niaouli oil | 1.0 |
| (13) | Purified water | Balance |

The invention claimed is:

1. A method of ameliorating wrinkles comprising administering to a subject having wrinkles a formulation comprising one or more components selected from the group consisting of rose oxide, citronellyl acetate, and niaouli oil, wherein the one or more components is present in the formulation at a concentration of 0.0001 to 0.1% by weight.

2. The method of claim 1, wherein the one or more components is present in the formulation at a concentration of 0.001 to 0.01% by weight.

3. The method of claim 1, wherein the one or more components is present in the formulation at a concentration of 0.005 to 0.01% by weight.

* * * * *